US008111891B2

(12) United States Patent
Ichihara (10) Patent No.: US 8,111,891 B2
(45) Date of Patent: Feb. 7, 2012

(54) X-RAY CT APPARATUS, MYOCARDIAL PERFUSION INFORMATION GENERATING SYSTEM, X-RAY DIAGNOSTIC METHOD AND MYOCARDIAL PERFUSION INFORMATION GENERATING METHOD

(75) Inventor: Takashi Ichihara, Nagoya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 944 days.

(21) Appl. No.: 12/044,432

(22) Filed: Mar. 7, 2008

(65) Prior Publication Data
US 2008/0273782 A1 Nov. 6, 2008

(30) Foreign Application Priority Data
Mar. 9, 2007 (JP) ................ P2007-059756

(51) Int. Cl.
*G06K 9/00* (2006.01)
(52) U.S. Cl. ............ 382/131; 378/4; 600/425; 600/431
(58) Field of Classification Search ............... 378/4–20; 382/128, 130–132; 600/407, 425, 431
See application file for complete search history.

(56) References Cited

U.S. PATENT DOCUMENTS
2005/0277830 A1 12/2005 Ichihara
2006/0241402 A1 10/2006 Ichihara et al.

FOREIGN PATENT DOCUMENTS
| DE | 196 47 701 A1 | 5/1998 |
| EP | 1 323 434 A2 | 7/2003 |
| EP | 1 604 612 A1 | 12/2005 |
| JP | 2006-21022 | 1/2006 |
| JP | 2006-247388 | 9/2006 |
| WO | WO 00/64353 | 11/2000 |
| WO | WO 02/079776 A2 | 10/2002 |
| WO | WO 2006/086442 A2 | 8/2006 |

OTHER PUBLICATIONS

Richard T. George, et al., "Multidetector Computed Tomography Myocardial Perfusion Imaging During Adenosine Stress", Journal of the American College of Cardiology, XP005519506, vol. 48, No. 1, ISSN: 0735-1097, 2006, pp. 153-160.
Keith M. Stantz, et al., "In Vivo Regional Myocardial Perfusion Measurements in a Porcine Model by ECG-Gated Multi-Slice Computed Tomography", Proceedings of Spie, vol. 5031, XP002344670, ISSN: 0277-786X, 2003, pp. 222-233.

*Primary Examiner* — Courtney Thomas
(74) *Attorney, Agent, or Firm* — Oblon, Spivak, McClelland, Maier & Neustadt, L.L.P.

(57) ABSTRACT

An X-ray CT apparatus has an image generating unit and a blood flow information acquiring unit. The image generating unit acquires projection data at rest and at non-rest from a myocardial part of an object into which contrast medium is injected continuously in a state in which each concentration of the contrast medium can be considered to be constant and reconstructs contrast CT image data at the rest and at the non-rest using the acquired projection data. The blood flow information acquiring unit obtains third blood flow information based in first blood flow information derived from the contrast CT image data at the rest and second blood flow information derived from the contrast CT image data at the non-rest.

12 Claims, 7 Drawing Sheets

X-RAY CT APPARATUS, MYOCARDIAL PERFUSION INFORMATION GENERATING SYSTEM, X-RAY DIAGNOSTIC METHOD AND MYOCARDIAL PERFUSION INFORMATION GENERATING METHOD

BACKGROUND OF THE INVENTION

1. Field of the Invention

The present invention relates to an X-ray CT (computed tomography) apparatus, a myocardial perfusion information generating system, an X-ray diagnostic method and a myocardial perfusion information generating method for generating myocardial perfusion information with continuously injecting a contrast medium.

2. Description of the Related Art

With a myocardial contrast examination using an X-ray CT apparatus, a contrast medium is injected into an object that is a patient, and contrast CT images are collected. Subsequently, moving images of coronary arteries, endocardial lumen wall, and so forth, are generated from the collected contrast CT images, and are employed for diagnosis.

Also, a blood flow dynamic state (perfusion) examination of the myocardium and a perfusion examination regarding organs such as within a brain tissue have been performed using an X-ray CT apparatus. With these perfusion examinations, attempting to generate a perfusion image by analyzing dynamic contrast CT data obtained from dynamic imaging by bolus injection for injecting a contrast medium in a short period has been conventionally studied.

However, normally, such perfusion imaging is not an isolated examination, but performed as part of a contrast examination. For example, in the event of a myocardial perfusion image, scanning for heart function analysis such as coronary arteries and endocardial lumen movement is also performed as well as scanning of a myocardial perfusion image. Accordingly, there is a problem that it takes a long time for scanning of a myocardial perfusion image, which results in increase of X-ray dosages for the object.

To such a problem, a technology to obtain blood flow information based on information including a coronary contrast CT image data and a myocardial contrast CT image data obtained by a scan for obtaining a myocardial image is devised without adding a scan for obtaining blood flow information to generate a myocardial perfusion image in more short time reducing a contrast medium injection volume to an object and exposure by X-ray.

This is a technology to extract the information related to a myocardial perfusion from a coronary contrast CT data and a myocardial contrast CT data by data processing for imaging since the information related to the myocardial perfusion serving as an index of a blood flow dynamic state on a myocardial region is included in the coronary contrast CT data and the myocardial contrast CT data acquired by a continuous contrast medium injection under a fixed condition. Specifically, during contrast medium is flowing with a constant concentration in a myocardial region and a coronary artery after static contrast medium injection into an object, a myocardial contrast CT image is obtained. Since a distribution image of contrast medium component obtained by subtracting the CT value of myocardium from the obtained myocardial contrast CT image has proportional relation to blood flow perfusion, the distribution image of contrast medium component is considered as a blood flow perfusion image indicating a relative blood flow perfusion (see, for example, Japanese Patent Application (Laid-Open) No. 2006-21022).

In addition, it is possible to convert a relative value of a myocardial blood flow image to an absolute value by calculating an unknown approximately using ECG synchronous CT image data acquired in a transitional period of concentration of contrast medium (see, for example, Japanese Patent Application (Laid-Open) No. 2006-247388). This allows generating a clinically-useful absolute value image of blood flow and a distribution image of local myocardial blood flow myocardium-wide.

As a related technology, the attempt to obtain a transforming function f(MBF) for transforming myocardial blood flow (MBF) to a ratio Cmyo/Ca between a concentration Ca of contrast medium in a left ventricle lumen of heart and a concentration Cmyo of contrast medium in blood of myocardium is performed (see, for example, George et al. "Multidetector Computed Tomography Myocardial Perfusion Imaging During Adenosine Stress", Journal of the American College of Cardiology, Vol. 48, No. 1, 2006).

As mentioned above, the technology to obtain blood flow information from the information such as coronary contrast CT image data and myocardial contrast CT image data obtained by a scan for obtaining a myocardial image is devised, it is preferable to obtain more myocardial perfusion information which is helpful in diagnosis.

SUMMARY OF THE INVENTION

The present invention has been made in light of the conventional situations, and it is an object of the present invention to provide an X-ray CT apparatus, a myocardial perfusion information generating system, an X-ray diagnostic method and a myocardial perfusion information generating method which can acquire myocardial perfusion information useful for diagnosis in a shorter period while reducing the amount of injection of a contrast medium as to an object and dosage due to X-ray.

The present invention provides an X-ray CT apparatus comprising: an image generating unit configured to acquire projection data at rest and projection data at non-rest from a myocardial part of an object into which contrast medium is injected continuously at the rest and at the non-rest respectively in a state in which each concentration of the contrast medium can be considered to be constant and reconstruct contrast CT image data at the rest and contrast CT image data at the non-rest using the acquired projection data at the rest and the acquired projection data at the non-rest respectively; and a blood flow information acquiring unit configured to obtain third blood flow information based in first blood flow information derived from the contrast CT image data at the rest and second blood flow information derived from the contrast CT image data at the non-rest, in an aspect to achieve the object.

The present invention also provides a myocardial perfusion information generating system comprising: an image acquiring unit configured to acquire contrast CT image data at a rest and contrast CT image data at a non-rest of a myocardial part of an object into which contrast medium is injected continuously in a state in which each concentration of the contrast medium at the rest and at the non-rest can be considered to be constant respectively; and a blood flow information acquiring unit configured to obtain third blood flow information based in first blood flow information derived from the contrast CT image data at the rest and second blood flow information derived from the contrast CT image data at the non-rest, in an aspect to achieve the object.

The present invention also provides an X-ray diagnostic method comprising: acquiring projection data at rest and projection data at non-rest from a myocardial part of an object into which contrast medium is injected continuously at the rest and at the non-rest respectively in a state in which each concentration of the contrast medium can be considered to be constant and reconstructing contrast CT image data at the rest and contrast CT image data at the non-rest using the acquired projection data at the rest and the acquired projection data at the non-rest respectively; and obtaining third blood flow information based in first blood flow information derived from the contrast CT image data at the rest and second blood flow information derived from the contrast CT image data at the non-rest, in an aspect to achieve the object.

The present invention also provides a myocardial perfusion information generating method comprising: acquiring contrast CT image data at a rest and contrast CT image data at a non-rest of a myocardial part of an object into which contrast medium is injected continuously in a state in which each concentration of the contrast medium at the rest and at the non-rest can be considered to be constant respectively; and obtaining third blood flow information based in first blood flow information derived from the contrast CT image data at the rest and second blood flow information derived from the contrast CT image data at the non-rest, in an aspect to achieve the object.

The X-ray CT apparatus, the myocardial perfusion information generating system, the X-ray diagnostic method and the myocardial perfusion information generating method as described above make it possible to acquire myocardial perfusion information useful for diagnosis in a shorter period while reducing the amount of injection of a contrast medium as to an object and dosage due to X-ray.

DESCRIPTION OF THE PREFERRED EMBODIMENTS

An X-ray CT apparatus, a myocardial perfusion information generating system, an X-ray diagnostic method and a myocardial perfusion information generating method according to the present invention will now be described in further detail below with reference to embodiments in conjunction with the accompanying drawings.

Figure 1:
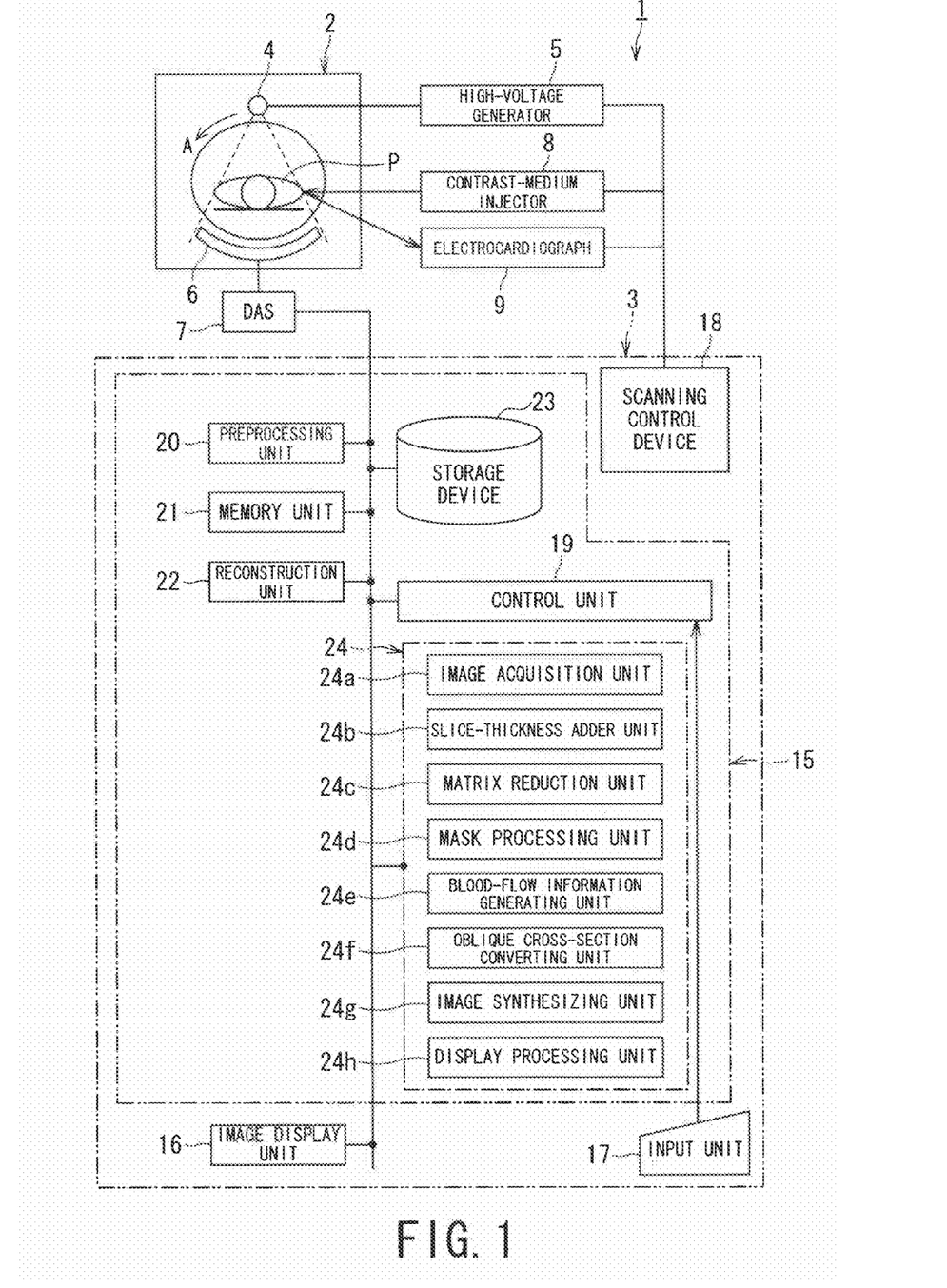
FIG. 1 is a configuration diagram illustrating an X-ray CT apparatus according to an embodiment of the present invention.

FIG. 1 is a configuration diagram illustrating an X-ray CT apparatus according to an embodiment of the present invention.

An X-ray CT apparatus 1 includes a gantry unit 2 and a computer device 3. The gantry unit 2 includes an X-ray tube 4, a high-voltage generator 5, an X-ray detector 6, a DAS (Data Acquisition System) 7, a contrast-medium injector 8, and an electrocardiograph 9. The X-ray tube 4 and the X-ray detector 6 are mounted at positions facing each other sandwiching an object P in an unshown rotating ring consecutively rotating at a high speed.

The X-ray CT apparatus 1 has a function to generate contrast CT image data of the object P under administration of contrast medium and generate a blood flow image and blood flow information from the generated contrast CT image data. Here, the principle and a method for generating a blood flow image and blood flow information will be described.

Figure 2:
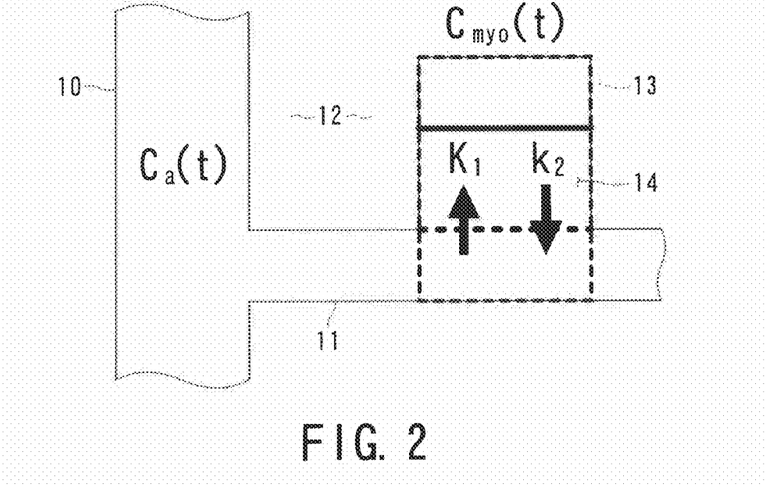
FIG. 2 is a diagram illustrating a model of the behavior of a contrast medium in the heart, within the myocardium, and within a coronary artery of an object.

FIG. 2 is a diagram illustrating a model of the behavior of a contrast medium in the heart, within the myocardium, and within a coronary artery of an object.

The unshown aorta branches off to a coronary artery 10, and the coronary artery 10 further branches off to a capillary 11, within the object P. The capillary 11 is introduced into the myocardium 12, and the myocardium 12 comprises the capillary 11 and a myocardial cell 13. The myocardial cell 13 includes a region referred to as a framework 14, and is configured such that the blood can move in and out between the framework 14 and the capillary 11.

Consequently, when a contrast medium is injected into the object P, the contrast medium is led from the aorta to the coronary artery 10 along with the blood, and led from the coronary artery 10 to the capillary 11. Furthermore, when the contrast medium flows along with the blood within the capillary 11, and reaches the myocardial cell 13, part of the contrast medium flows in the framework 14 within the myocardial cell 13 from the capillary 11. Moreover, the part of the blood flowed in the framework 14 within the myocardial cell 13 flows out of the myocardial cell 13 and moves in the capillary 11 again.

Accordingly, the concentration of the contrast medium in blood within the aorta or coronary artery 10 and the concentration of the contrast medium in blood within the myocardial cell 13 or capillary 11 exhibit different values, and change over time due to movement of the contrast medium. The concentration of the contrast medium in blood within each portion of the object P is determined by a transitional constant at the time of the contrast medium flowing in the framework 14 within the myocardial cell 13 from the capillary 11, and a transitional constant at the time of the contrast medium flowing in the capillary 11 from the framework 14 within the myocardial cell 13.

More specifically, let us say that the concentration of the contrast medium within the LV (left ventricular) lumen or the coronary artery in time t is Ca(t), a region included in the myocardium 12, which includes the capillary 11 and myocardial cell 13, is a unit region, the concentration of the contrast medium within the blood in the myocardium 12 (the average concentration of the contrast medium within the capillary 11 and myocardial cell 13) is Cmyo(t), a transitional constant at the time of the contrast medium flowing in the framework 14 within the myocardial cell 13 from the capillary 11 is K1, and a transitional constant at the time of the contrast medium flowing out of the capillary 11 to the framework 14 within the myocardial cell 13 is k2, Ca(t) and Cmyo(t) are determined by the transitional constant K1 and the transitional constant k2.

Figure 3:
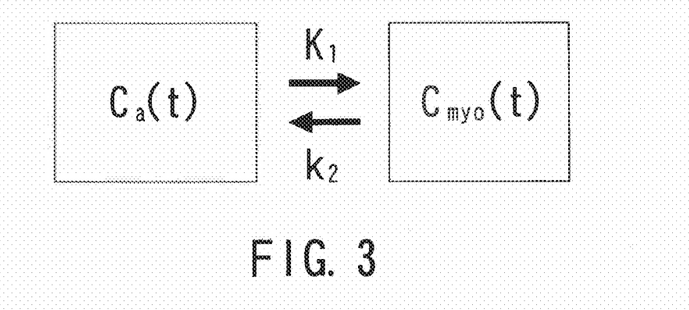
FIG. 3 is a diagram conceptually representing the model illustrated in FIG. 2 using parameters.

FIG. 3 is a diagram conceptually representing the model illustrated in FIG. 2 using parameters.

As illustrated in FIG. 3, while the contrast medium having the concentration Ca(t) and the amount proportional to the transitional constant K1 moves in the framework 14 of the myocardial cell 13 from the capillary 11, the contrast medium having the concentration Cmyo(t) and the amount proportional to the transitional constant k2 moves in the capillary 11 from the framework 14 of the myocardial cell 13 at certain time t. Subsequently, the concentration Ca(t) and concentration Cmyo(t) of the contrast medium following movement are determined the transitional constant K1 and transitional constant k2.

Accordingly, the concentration Cmyo(t) of the contrast medium within the myocardium 12 at a certain time t can be represented by the difference between the amount of the contrast medium flowing in the framework 14 and the amount of the contrast medium flowing out of the framework 14, thereby satisfying the following Expression (1).

$$\frac{dC_{myo}(t)}{dt} = K_1 C_a(t) - k_2 C_{myo}(t) \quad (1)$$

On the other hand, heretofore, it has been known that when a contrast medium is injected statically into the object P in accordance with a certain condition, a state in which the concentrations Ca(t) and Cmyo(t) of the contrast medium in blood within a coronary artery (or in a LV lumen) and the myocardium 12 are considered to be constant respectively emerges, i.e., a constant concentration period emerges.

Consequently, in the event that X-ray CT data is acquired synchronously with an electrocardiogram in the period in which each of the concentration Cmyo(t) of the contrast medium within the myocardial region and the concentration Ca(t) of the contrast medium in the coronary artery (or the LV lumen) is constant or considered to be constant because of a gradual increasing rate, a blood flow image is readily generated with various types of processing using the X-ray CT data following collection. Consequently, the contrast-medium injector 8 is configured so as to inject the contrast medium having a predetermined amount rate per time into the object P in accordance with a certain condition, and so as to obtain a state in which the concentration Ca(t) and concentration Cmyo(t) of the contrast medium within the coronary artery (or the LV lumen) and myocardial portion are considered to be constant.

Note that the condition for injecting the contrast medium is experientially determined such that the concentration Ca(t) of the contrast medium within the coronary artery or the LV becomes constant during collection of X-ray CT data, so some difference exists in injection speed. The recommended conditions such as injection speed at the time of static injection of the contrast medium are described in documents such as "Study of Optimal Contrast Examination Method in Herical Scanning CT", by Atsusi Yamachi and Tadashi Wako, Japan-Germany Medical Reports Vol. No. 2, 1995, for example.

Further, an period in which the concentration Ca(t) of the contrast medium within the coronary artery or the LV is not constant can be also employed for generation of a blood flow image if a state in which change-of-time of the concentration Ca(t) of the contrast medium within the coronary artery or the LV is considered to be constant and shows linear properties is satisfied. Therefore, the condition for injecting the contrast medium is adjusted by the contrast-medium injector 8 such that change-of-time of the concentration Ca(t) of the contrast medium within the coronary artery or the LV becomes constant.

Now, in the event of defining a concentration transition period Tt as a period from immediately after starting of continuously injection of a contrast medium into an object P until the contrast medium injected reaches to the myocardium, increases, and will be in a state where it can be considered that a concentration Ca(t) of the contrast medium within the coronary artery or the LV and a concentration Cmyo(t) of the contrast medium within a myocardial region are saturated in a constant value respectively, the concentration Cmyo(t) of the contrast medium within the myocardial region is sufficiently smaller than the concentration Ca(t) of the contrast medium within the coronary artery, particularly within the left ventricular lumen during a concentration transition period Tt, so an approximate expression shown in Expression (2) can be satisfied.

$$K1Ca(t) \gg k2Cmyo(t) \quad (2)$$

Accordingly, with the concentration transition period Tt in which Expression (2) is satisfied, Expression (1) can be approximated as shown in Expression (3).

$$\frac{dCmyo(t)}{dt} \cong K1 \cdot Ca(t) \quad (3)$$

Furthermore, upon both sides of Expression (3) being subjected to temporal integration, Expression (4) can be obtained.

$$Cmyo(t) \cong K1 \int_0^t Ca(\tau)d\tau \quad (4)$$

Consequently, Expression (5) can be derived from Expression (4).

$$K1 \cong \frac{\int_0^t Ca(\tau)d\tau}{Cmyo(t)} \quad (5)$$

Expression (5) indicates that in the event that the concentration Ca(t) of the contrast medium within the coronary artery, particularly, within the left ventricular lumen and the concentration Cmyo(t) of the contrast medium of a specific myocardial site A (the myocardial site of the left ventricle myocardium in the event that the coronary artery is a blood flow within the left ventricular lumen, hereinafter referred to as specific myocardial site) can be obtained, K1 in the specific myocardial site A can be obtained using a technique generally called as the Patlak plot method (graphical plot method).

In the event that the concentration Cmyo(t) of the contrast medium within the myocardial portion is considered to be constant, the left side of Expression (1) becomes zero, so Expression (6) can be obtained.

$$\frac{dCmyo(t)}{dt} = 0 \qquad (6)$$

Rewriting Expression (1) as Expression (7) from Expression (6), $$K1 \cdot Ca(t) - k2 \cdot Cmyo(t) = 0 \qquad (7)$$

Furthermore, modifying Expression (7) obtains Expression (8).

$$K1 = \frac{k2 \cdot Cmyo(t)}{Ca(t)} \qquad (8)$$

In Expression (8), when the concentration Ca(t) of the contrast medium within the coronary artery is considered to be constant, the transitional constant K1 is proportional to the concentration Cmyo(t) of the contrast medium within the myocardial portion, as shown in Expression (9).

$$K1 \propto Cmyo(t) \qquad (9)$$

Furthermore, with a value representing the fraction of the contrast medium within the blood flow concentration (extraction fraction) as E, and blood perfusion [ml/100 g/min], which is a blood flow rate in unit time and unit weight, serving as the index of perfusion, as F, it has been known that the transitional constant K1 has a relation of K1=E×F.

Accordingly, as illustrated in Expression (10), the concentration Cmyo(t) of the contrast medium within the myocardial portion is proportional to the blood perfusion F within the myocardial portion.

$$Cmyo(t) \propto F \qquad (10)$$

That is to say, it is known that the concentration Cmyo(t) of the contrast medium within the myocardial portion indicates the relative value of the blood perfusion F. Accordingly, if the concentration Cmyo(t) of the contrast medium within the myocardial portion can be obtained, the relative value of the blood perfusion F can be known.

Now, the CT value of myocardial contrast CT image data to be obtained by injecting the contrast medium is equal to sum of the CT value of only the myocardium serving as a myocardial tissue component and the CT value of image of a contrast medium component. Accordingly, if the CT value of only the myocardial portion is subtracted from the myocardial contrast CT image data, the concentration Cmyo(t) of the contrast medium and the ratio of concentration Cmyo(t)/Ca(t) of the contrast medium within the myocardial portion having a proportional relation to the CT value of image of the contrast medium component can be obtained.

That is to say, it can be considered that each of a concentration Cmyo(t) of the contrast medium on a myocardial region and a concentration Ca(t) of the contrast medium in a LV can be treated as a parameter which is equivalent to a CT value. Here, a concentration Cmyo(t) of the contrast medium on a myocardial region and a concentration Ca(t) of the contrast medium in a LV are treated as CT values of an image of contrast medium component.

Figure 4:
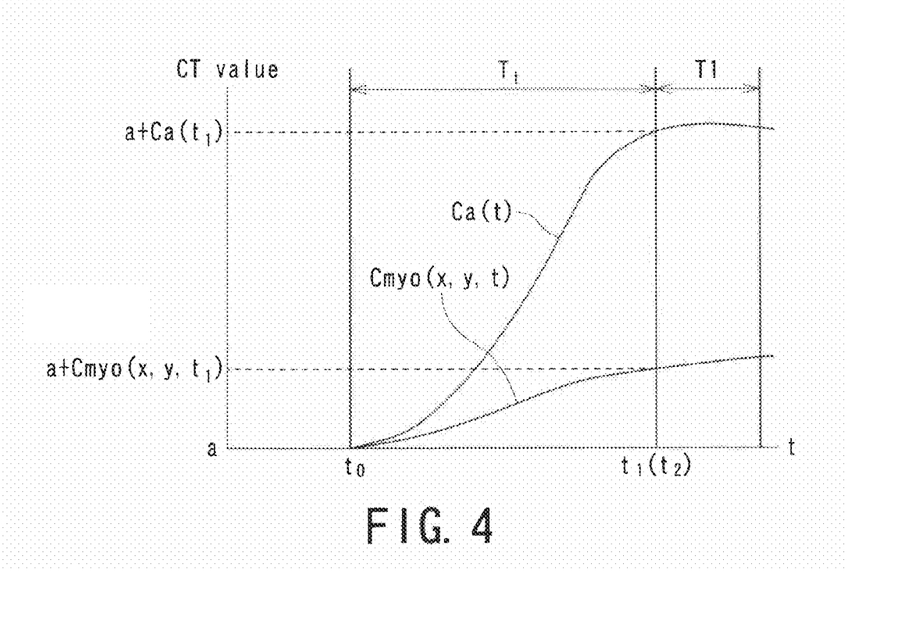
FIG. 4 is a diagram illustrating the temporal concentration variation of a contrast medium and CT values of contrast CT image data in a LV and a myocardial portion due to continuous static injection of the contrast medium into an object using the contrast-medium injector illustrated in FIG. 1.

FIG. 4 is a diagram illustrating the temporal concentration variation of a contrast medium and CT values of contrast CT image data in a LV and a myocardial portion due to continuous static injection of the contrast medium into an object using the contrast-medium injector 8 illustrated in FIG. 1.

In FIG. 4, the vertical axis represents a CT value corresponding to concentration of the contrast medium, and the horizontal axis represents time t. Moreover, the curved lines are data indicating change-of-time of the concentration Ca(t) of the contrast medium within the LV and data indicating change-of-time of the concentration Cmyo(t) of the contrast medium within the myocardial portion made up of the myocardial cell 13 and capillary 11.

As shown in FIG. 4, when contrast medium is injected at time t0, a concentration Ca(t) of the contrast medium in a LV and a concentration Cmyo(x, y, t) of the contrast medium at a location (x, y) on a short axis crossing image in a myocardial region increase gradually. Then, after a transitional period Tt of concentration of the contrast medium when the concentration Ca(t) of the contrast medium in the LV and the concentration Cmyo (x, y, t) of the contrast medium at a location (x, y) on the myocardial region increase, the period T1 when the concentration Ca(t) of the contrast medium in the LV and the concentration Cmyo(t) of the contrast medium at the location (x, y) on the myocardial region are constant respectively or their increase rates are slow is obtained.

This trend is similar at rest and at non-rest including with drug stress, for example, such as a case of giving a drug for stress. That is, at rest, the period T1 when the concentration Ca(t) of the contrast medium in the LV and the concentration Cmyo(t) of the contrast medium on the myocardial region are constant respectively or their increase rates are slow starts at a time t1. On the other hand, with drug stress, the period T1 when the concentration Ca (t) of the contrast medium in the LV and the concentration Cmyo(t) of the contrast medium on the myocardial region are constant respectively or their increase rates are slow starts at a time t2.

Further, "a" is a CT value on the myocardial region and in the LV under a condition without giving the contrast medium. Note that, although there is a case that the CT value a1 on the myocardial region and the CT value a2 in the LV are different rigorously, here, it is assumed to be a1=a2=a. This CT value a is a constant value determined by a physical condition.

Here, there is a flow reserve as important diagnosis information to evaluate a myocardial viability. The flow reserve is the increase rate of blood flow between at rest and at non-rest such as with drug stress, it is obtained from the concentration Ca(t) of the contrast medium in the LV blood pool and the concentration Cmyo(t) of the contrast medium on the myocardial region.

Figure 5:
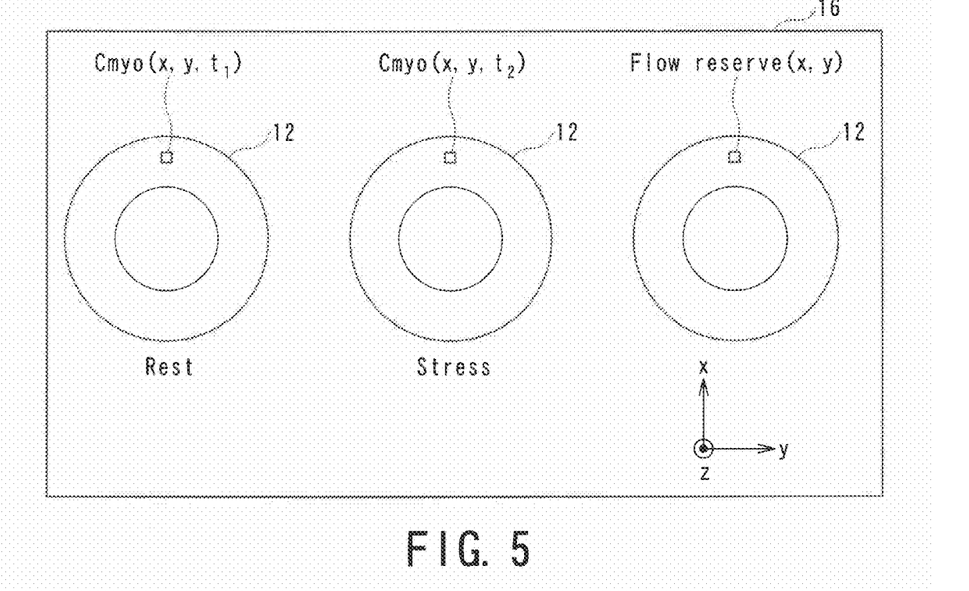
FIG. 5 is a diagram showing a definition of parameters used for calculating a flow reserve and an example of displaying blood flow information in the X-ray CT apparatus shown in FIG. 1.

FIG. 5 is a diagram showing a definition of parameters used for calculating a flow reserve and an example of displaying blood flow information in the X-ray CT apparatus 1 shown in FIG. 1.

As shown in FIG. 5, x axis and y axis to be orthogonal mutually are set on a myocardial short axis crossing image at rest and with drug stress and z axis is set in the direction which is orthogonal to the myocardial short axis crossing image. At rest, the time t when the concentration Ca(t) of the contrast medium in the LV and the concentration Cmyo(t) of the contrast medium on the myocardial region are considered to be constant respectively is set to t1 and with drug stress, the time t when the concentration Ca(t) of the contrast medium in the LV and the concentration Cmyo(t) of the contrast medium on the myocardial region are considered to be constant respectively is set to t2.

Then, a flow reserve (x, y) at a location (x, y) on the myocardial region can be obtained when the concentration Cmyo (x, y, t1) of the contrast medium on the myocardial region at rest at time t1 and the concentration Cmyo (x, y, t2) of the contrast medium on the myocardial region with drug stress at time t2 are obtained respectively by subtracting the CT value a of the myocardial region from myocardial contrast CT image data. Now that, rigorously, a Cmyo(x, y, t1) is a value which is proportional to the concentration of the contrast medium on the myocardial region at rest and a Cmyo(x, y, t2) is a value which is proportional to the concentration of the contrast medium on the myocardial region with drug stress.

A flow reserve (x, y) is provided by the ratio between a myocardial blood flow (MBF) with drug stress and a MBF at rest. When a MBF is sufficiently-small, it is known that a MBF has proportional relation (linear correlation) to the ratio Cmyo (x, y, t)/Ca(t) between the concentration Cmyo (x, y, t) of the contrast medium on the myocardial region and the concentration Ca(t) of the contrast medium in the LV or a transition constant K1.

Therefore, a flow reserve (x, y) can be obtained by the expression (11), when it is assumed that a location (x, y) doesn't move between time t1 and time t2, in the case of a sufficiently-small MBF.

flow reserve(x,y)=

$$\{Cmyo(x,y,t2)/Ca(t2)\}/\{Cmyo(x,y,t1)/Ca(t1)\} \quad (11)$$

When the amount of change of the concentration Ca(t) of the contrast medium in the LV is negligible between time t1 and time t2, the flow reserve (x, y) can be obtained by the expression (12) more easily.

flow reserve(x,y)=

$$Cmyo(x,y,t2)/cmyo(x,y,t1) \quad (12)$$

When a MBF is not sufficiently-small, the MBF doesn't have proportional relation to the ratio Cmyo(x, y, t)/Ca(t) between the concentration Cmyo(x, y, t) of the contrast medium on the myocardial region and the concentration Ca(t) of the contrast medium in the LV necessarily. In this case, a flow reserve (x, y) can be obtained by using a transforming function f to convert the MBF to the ratio Cmyo(x, y, t)/Ca(t) between the concentration Cmyo(x, y, t) of contrast medium on the myocardial region and the concentration Ca(t) of the contrast medium in the LV with higher accuracy.

Figure 6:
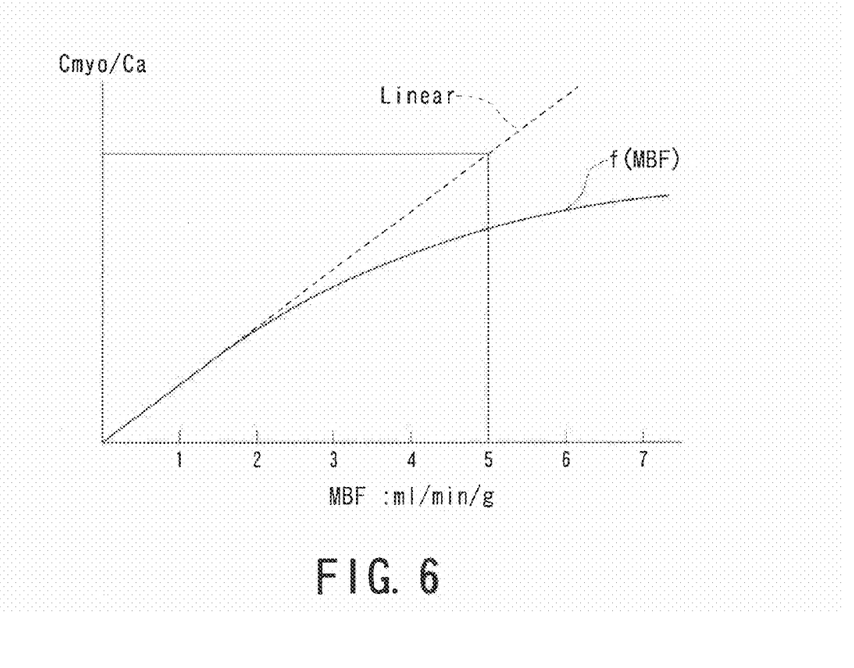
FIG. 6 is a diagram indicating a transforming function f for transforming a MBF into a ratio Cmyo(x, y, t)/Ca(t) between a concentration Cmyo (x, y, t) of the contrast medium in the myocardial portion and a concentration Ca(t) of the contrast medium in the LV.

FIG. 6 is a diagram indicating a transforming function f for transforming a MBF into a ratio Cmyo(x, y, t)/Ca(t) between a concentration Cmyo (x, y, t) of the contrast medium in the myocardial portion and a concentration Ca(t) of the contrast medium in the LV.

In FIG. 6, the horizontal axis represents a MBF (ml/min/g), and the vertical axis represents a ratio Cmyo(x, y, t)/Ca(t) between a concentration Cmyo (x, y, t) of the contrast medium in the myocardial portion and a concentration Ca(t) of the contrast medium in the LV.

When a MBF is sufficiently-small, as shown by the dot-line in FIG. 6, a flow reserve (x, y) can be obtained as having a linear correlation between a MBF and the concentration ratio Cmyo(x, y, t)/Ca(t) of the constant medium. However, when a MBF is increasing, the trend which the concentration ratio Cmyo(x, y, t)/Ca(t) of the contrast medium is saturated to deviate from the line showing the linear correlation may be shown, that is, there is a case to show non-linear correspondence relation. For example, in case that a MBF=5 to 60 (ml/min/g), when the MBF and the concentration ratio Cmyo (x, y, t)/Ca(t) of the contrast medium are assumed to have a liner relation, the error becomes large. Then, by using the transforming function f(MBF), as shown by the solid line in FIG. 6, which convert a MBF to the concentration ratio Cmyo (x, y, t)/Ca(t) of the contrast medium or a transition constant K1, even if a MBF and the concentration ratio of Cmyo(x, y, t)/Ca(t) of the contrast medium have no linear relation, a MBF and a flow reserve (x, y) can be obtained from the concentration ratio Cmyo(x, y, t)/Ca(t) of the contrast medium with higher accuracy.

When a flow reserve (x, y) is obtained by using the transforming function f(MBF), the flow reserve (x, y) can be obtained by the expression (13).

flow reserve(x,y)=

$$F\{Cmyo(x,y,t2)/Ca(t2)\}/F\{Cmyo(x,y,t1)/Ca(t1)\} \quad (13)$$

Note that in Expression (13), F=f−1 wherein f−1 is the inverse function of the transforming function f(MBF). In other words, F(Cmyo(x, y, t)/Ca(t)) is a function for transforming a ratio of concentration Cmyo(x, y, t)/Ca(t) of the contrast medium or a transitional constant K1 into a MBF.

A transforming function f(MBF) can be obtained preliminarily with an arbitrary method. For example, it can be obtained based on blood flow information obtained from a same object or another object through a scan by the X-ray CT apparatus 1. A transforming function f(MBF) can be also obtained from blood flow information obtained from a same or another object by another image diagnostic apparatus such as PET (positron emission computed tomography). Here, it is considered that there is a case to meet required accuracy by using a transforming function f(MBF) which is obtained by using not only a human but also a dog and a pig as another object. A method for obtaining a transforming function f(MBF) is described on George et al. "Multidetector Computed Tomography Myocardial Perfusion Imaging During Adenosine Stress", Journal of the American College of Cardiology, Vol. 48, No. 1, 2006 in detail.

For example, a flow reserve (x, y) of a normal myocardial region has a value over 3 to 4. Alternatively, a flow reserve (x, y) on a region where has a coronary stenosis has a lower value than a normal value depending on degree of stenosis. Therefore, degree of myocardial damage by ischemia of a target myocardial region can be evaluated by a value of flow reserve (x, y).

Noise superimposing on the concentration Cmyo(x, y, t1) of the contrast medium on the myocardial region can be suppressed by smoothing the concentration Cmyo(x, y, t1) of the contrast medium on the myocardial region at rest at time t1 in a direction (x, y) on a myocardial short axis crossing image. On the contrary, since high-resolution is required in a direction (x, y) on a myocardial short axis crossing image in many cases on the concentration Cmyo(x, y, t2) of the contrast medium on the myocardial region with drug stress at time t2, in this case, smoothing isn't performed. Alternatively, on z direction perpendicular to a myocardial short axis crossing image, the concentration Cmyo(x, y, z, t1) of the contrast medium on the myocardial region at rest at time t1 and the concentration Cmyo(x, y, z, t2) of the contrast medium on the myocardial region with drug stress at time t2 can be smoothed respectively for suppressing noise.

Figure 7:
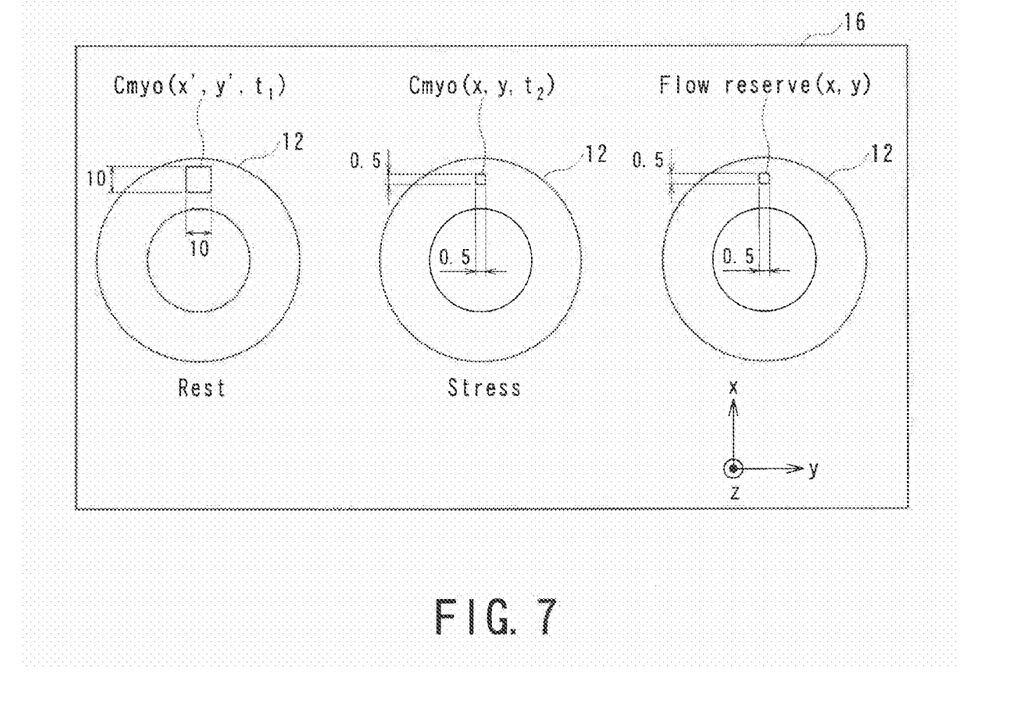
FIG. 7 is a diagram showing a method for calculating a flow reserve (x, y) by smoothing a concentration Cmyo (x, y, t1) of the contrast medium in a myocardial region at a time t1 during rest and an example of displaying blood flow information in the X-ray CT apparatus shown in FIG. 1.

FIG. 7 is a diagram showing a method for calculating a flow reserve (x, y) by smoothing a concentration Cmyo (x, y, t1) of the contrast medium in a myocardial region at a time t1 during rest and an example of displaying blood flow information in the X-ray CT apparatus 1 shown in FIG. 1.

FIG. 7 shows a myocardial short axis crossing image. As shown in FIG. 7, for example, when the concentration Cmyo (x, y, z, t1) of the contrast medium on the myocardial region is obtained as data in a voxel of 0.5 mm×0.5 mm×0.5 mm at rest at time t1, the concentration Cmyo (x, y, z, t1) of the contrast medium on the myocardial region is averaged in the directions x, y, z so as to be data in a voxel of 10 mm×10 mm×10 mm. This allows noise of the concentration Cmyo(x, y, z, t1) of the contrast medium on the myocardial region at rest to be suppressed.

Alternatively, on the concentration Cmyo(x, y, z, t2) of the contrast medium on the myocardial region obtained as a data in a voxel of 0.5 mm×0.5 mm×0.5 with drug stress at time t2, averaging in the directions x, y isn't performed to ensure the resolutions of x, y directions. The concentration Cmyo(x, y, z, t2) of the contrast medium on the myocardial region with drug stress can be smoothed in only z direction in which high resolution is not required. For example, smoothing in z direction is performed by averaging the concentration Cmyo(x, y, z, t2) of the contrast medium on the myocardial region so as to be approximately 2 to 4 mm/pixel. That is, for example, the concentration Cmyo(x, y, z, t2) of the contrast medium on the myocardial region with drug stress is averaged in only z direction so as to be data in a voxel of 0.5 mm×0.5 mm×2 mm.

When a flow reserve (x, y) is obtained from the smoothed concentration Cmyo(x'y', z', t1) of the contrast medium on the myocardial region at rest and the concentration Cmyo(x, y, z'', t2) of the contrast medium on the myocardial region smoothed in only z direction, noise superimposing on the concentration Cmyo(x, y, z, t1) of the contrast medium on the myocardial region at rest is reduced and smooth data group of flow reserve (x, y) can be obtained.

By the way, in the event that the concentration Ca(t) of the contrast medium within the coronary artery is not considered to be constant, Expression (9) cannot be derived from Expression (8). However, in the event that the change-of-time rate of the concentration Ca(t) of the contrast medium within the coronary artery is constant, or in the event that there are linear properties between the concentration and CT value of the contrast medium, a correction coefficient is obtained based on the change-of-time rate of the contrast medium concentration within this coronary artery, and the blood flow relative image of the contrast medium component can be corrected using the obtained correction coefficient. For example, as shown in Expression (14), let us say that the proportion between the concentration Ca(t) of the contrast medium within the coronary artery at certain time t0 serving as a reference and the concentration Ca(t) of the contrast medium within the coronary artery at time t is a correction coefficient $\alpha(t)$, and correction can be performed by multiplying the CT value of the blood flow relative image of the contrast medium component by the correction coefficient $\alpha(t)$.

$$\alpha(t)=Ca(t)/Ca(t0) \qquad (14)$$

Furthermore, in Expression (5), the contrast medium concentration Ca(t) within the coronary artery such as the left ventricular lumen and the contrast medium concentration Cmyo(t) within the specific myocardial site A at time t during the concentration transition period Tt can be obtained from the electrocardiogram-synchronous CT image at the specific site A collected during the concentration transition period Tt as described above. Accordingly, the value of K1 at the specific myocardial site A can be obtained.

Now, let us say that the value of K1 at the specific myocardial site A is K1$a$, and the relative value R of the blood flow perfusion F at the specific myocardial site A obtained as a blood flow relative image is Ra. In this case, the relation of K1=E×F is satisfied as described above, so the relative value R of the blood flow perfusion F at the corresponding site can be converted into the absolute value of the blood flow perfusion F by multiplying the relative value R of the blood flow perfusion F at the corresponding site by K1$a$/(E×Ra). In other words, a blood flow relative image can be converted into a blood flow absolute image (also referred to as a blood flow value image) by considering K1$a$/(E×Ra) as a correction value, and correcting the blood flow relative image with the correction value. In this case, K1$a$ may be considered to be a blood flow by setting 1.0 to E.

Note that K1$a$/(E×Ra) serving as a correction value represents the change rate of the contrast medium concentration obtained based on multiple CT images during the concentration transition period.

Furthermore, there is a correlation such as continuity of value and so forth between the intensity of the blood flow absolute image at the corresponding site and that of the image of the myocardial portion in the tomograph of another myocardial perfusion, so with the entire myocardial tomograph, the relative R of the blood flow perfusion F can be converted into the absolute value of the blood flow perfusion F by multiplying the relative value R of the blood flow perfusion F at another myocardial cross-section by K1$a$/(E×Ra).

In other words, the blood flow relative image over the entire myocardium obtained during the constant concentration period can be converted into a blood flow absolute image by obtaining a value relation with the myocardial image at the same slice position obtained during the constant concentration period using the myocardial blood flow absolute image obtained during the concentration transition period. Thus, the blood flow image at the myocardium is converted from the relative value to an absolute value, thereby obtaining the distribution image of the absolute value of the local myocardial blood flow over the entire myocardium.

Then, each element of the X-ray CT apparatus 1 will be described in detail.

The contrast-medium injector 8, which is controlled by a control signal from the computer device 3, has a function for continuously injecting a contrast medium into the object P in accordance according to certain conditions. The contrast-medium injector 8 can control the amount and concentration of the contrast medium to be injected into the object P based on the behavior of the contrast medium within the object P.

On the other hand, the electrocardiograph 9 is connected to unshown electrodes connected to the object P. The electrocardiograph 9 has a function to detect an electrocardiogram signal (ECG signal) via the electrodes from the object P, generate an electrocardiogram of the object P from the detected ECG signal, and provides this to the computer device 3.

The high-voltage generator 5 is configured so as to supply a tube current or tube voltage to the X-ray tube 4 synchronously with the electrocardiogram in accordance with a control signal from the computer device 3, and so as to detect X-rays transmitting the object P using the X-ray detector 6, while the concentration Cmyo(t) and Ca(t) of the contrast medium within the coronary artery and the myocardial portion are constant or have linear properties. Furthermore, the X-ray detection signal detected by the X-ray detector 6 is provided to the DAS 7 so as to be digitized, and provided to the computer device 3.

Further, in order to know the timing at which the contrast medium passes through the portions such as the left ventricular lumen and so forth and reaches the myocardium, the X-ray CT apparatus 1 includes a function for performing dynamic collection of X-ray data from an arbitrary slice position on the specific myocardial site during the transition period to monitor the specific myocardial site. Dynamically collected data in the specific myocardial site is also given to the computer device 3 via the DAS 7 during this transition period.

Note that a technique example for finding the timing at which the contrast medium reaches the myocardium, and the concentration transition period Tt is changed to the interval T1 (constant concentration period), is disclosed in Japanese Unexamined Patent Application Publication No. 2003-245275.

More specifically, a technique is disclosed for automatically setting the timing at which the contrast medium reaches the myocardium using an optional method such as a method for determining whether or not the contrast medium concentration (or a CT value) reaches a predetermined threshold value, a method for converting the contrast medium concentration (or a CT value) into a graph, and determining whether or not the tangential gradient angle of the graph reaches a predetermined angle, a method for converting the contrast medium concentration (or a CT value) into a graph, and determining whether or not the graph reaches a peak, or the like. However, even without employing this technique, an arrangement may be made wherein an electrocardiogram-synchronous CT image or a change-of-time curve of the contrast medium concentration as illustrated in FIG. 4 is graphically displayed, and accordingly, the user can visually recognize the timing at which the contrast medium reaches the myocardium.

The computer device 3 comprises an image processing device 15, image display unit 16, input unit 17, and scanning control device 18. The scanning control device 18 has a function for providing a control signal to the high-voltage generator 5 and contrast-medium injector 8 to control these devices based on the electrocardiograms collected by the electrocardiograph 9, thereby executing collection of electrocardiogram-synchronous CT images.

In particular, the scanning control device 18 includes a function for detecting the timing at which the aforementioned concentration transition period Tt is changed to the interval T1 (constant concentration period) using an arbitrary method. An arrangement is made wherein pre-scanning for generating an electrocardiogram-synchronous CT image by stopping an unshown table on which the object lies and collecting data from the specific myocardial site A during the concentration transition period Tt, and real-scanning for generating an electrocardiogram-synchronous CT image by moving the unshown table and collecting data from the entire myocardium during the interval T1 serving as a constant concentration period, using the scanning control device 18, can be performed.

Moreover, the image processing device 15 comprises a control unit 19 serving as a core, a preprocessing unit 20 for converting raw data to be output from the DAS 7 into projection data via correction processing and the like, a memory unit 21 for storing the projection data, an image reconstruction unit 22 for reconstructing CT image data from the projection data, a storage device 23 for storing the CT image data, and a myocardial perfusion image generating system 24 for reading the CT image data from the storage device 23 so as to generate a myocardial perfusion image.

The myocardial perfusion image generating system 24 includes an image acquisition unit 24a, slice-thickness adder unit 24b, matrix reduction unit 24c, mask processing unit 24d, blood-flow information generating unit 24e, oblique cross-section converting unit 24f, image synthesizing unit 24g, and display processing unit 24h.

The image acquisition unit 24a includes a function for reading and acquiring myocardial contrast CT image data due to the contrast medium from the storage device 23, and a function for giving the acquired contrast CT image data to the other components of the myocardial perfusion image generating system 24.

The slice-thickness adder unit 24b has a function for receiving myocardial contrast CT image data from the image acquisition unit 24a, and adding the contrast CT values between the adjacent slices or averaging the values, thereby reducing the resolution of the contrast CT image data in the slice direction.

The matrix reduction unit 24c has a function for receiving myocardial contrast CT image data from the image acquisition unit 24a, and subjecting the contrast CT values to adding and averaging, thereby reducing the matrix of the myocardial contrast CT image data.

That is, smoothing processing can be performed for noise reduction as preprocessing to calculate flow reserve (x, y) by the slice-thickness adder unit 24b and the matrix reduction unit 24c.

The mask processing unit 24d has a function for receiving myocardial contrast CT image data from the image acquisition unit 24a, and subjecting the received CT image data to mask processing, thereby extracting a region where the blood flow of the myocardial portion exists.

The blood-flow information generating unit 24e has a function for generating a blood flow image and blood flow information such as flow reserve (x, y) in the flow region extracted by the mask processing unit 24d with the above-mentioned method. Specifically, the blood-flow information generating unit 24e includes a function for generating the image of the contrast medium component representing the relative value R of the blood perfusion F by subtracting the CT value of only the myocardium from the myocardial contrast CT image data in the blood flow region extracted by the mask processing unit 24d as a blood flow relative image, which is one of blood flow images, and a function for generating blood flow information such as flow reserve (x, y).

In addition, the blood-flow information generating unit 24e includes a function for obtaining the above-mentioned correction coefficient $\alpha(t)$ so as to correct the blood flow relative image of the contrast medium component and blood flow information such as flow reserve (x, y) in the event that the concentration $Ca(t)$ of the contrast medium within the coronary artery is not constant.

Further, the blood-flow information generating unit 24e includes a function for receiving the electrocardiogram-synchronous CT image at the specific site A collected during the concentration transition period Tt from the image acquisition unit 24a, and obtaining the value of K1 at the above-mentioned specific myocardial site A, and a function for generating a blood flow absolute image by converting the relative value R of the blood flow perfusion F into the absolute value of the blood flow perfusion F using the obtained K1.

The oblique cross-section converting unit 24f has a function for converting the cross-section of a myocardial blood flow image and blood flow information such as flow reserve (x, y) generated by the blood-flow information generating unit 24e, and generating a cross-sectional image at an arbitrary cross-section, e.g., a circular cross-sectional image with the longitudinal direction of the myocardium serving as an axis thereof and/or blood flow information such as flow reserve (x, y) at an arbitrary cross-section.

The image synthesizing unit 24g has a function for synthesizing an image having a high resolution prior to the matrix reduction processing and adding the contrast CT value between slices, i.e., the image data of the mask region of the myocardial contrast CT image data received from the image acquisition unit 24a with the myocardial blood flow image and blood flow information generated by the blood-flow information generating unit 24e so as to generate a synthesized image, and superimposing both of the image or information and the data at the same position on a screen, each of which an arbitrary value such as transparency is adjusted so as to display both of the image or information and the data.

In other words, image synthesizing processing allows superimposed display of a blood flow image and blood flow information generated by the blood-flow information generating unit 24e. For example, values of flow reserve (x, y) which shows a increase ratio of myocardial blood flow between at rest and with drug stress can be displayed on the corresponding locations x, y on a contrast CT image as shown in FIG. 5 and FIG. 7. Image synthesizing processing may be performed so that values of flow reserve (x, y) are displayed on the myocardial region and a contrast CT image at rest or with drug stress is displayed on another region. A flow reserve (x, y) may be also fused in 3-dimensional display of a coronary artery.

The display processing unit 24h has a function for providing to the image display unit 16 image signals for displaying the respective images such as blood flow images, oblique cross-sectional images, and synthesized images, which are generated by the blood-flow generating unit 24e, oblique cross-section converting unit 24f, and image synthesizing unit 24g respectively, and a function for setting display conditions so as to visually recognize a blood flow image and blood flow information in each displayed image.

Moreover, the display processing unit 24h is configured so as to display images for instructing the settings of display conditions on the image display unit 16 at the time of setting image display conditions, and also so as to acquire instructions for image display conditions from the input unit 17.

Next, operation of the X-ray CT apparatus 1 will be described.

Figure 8:
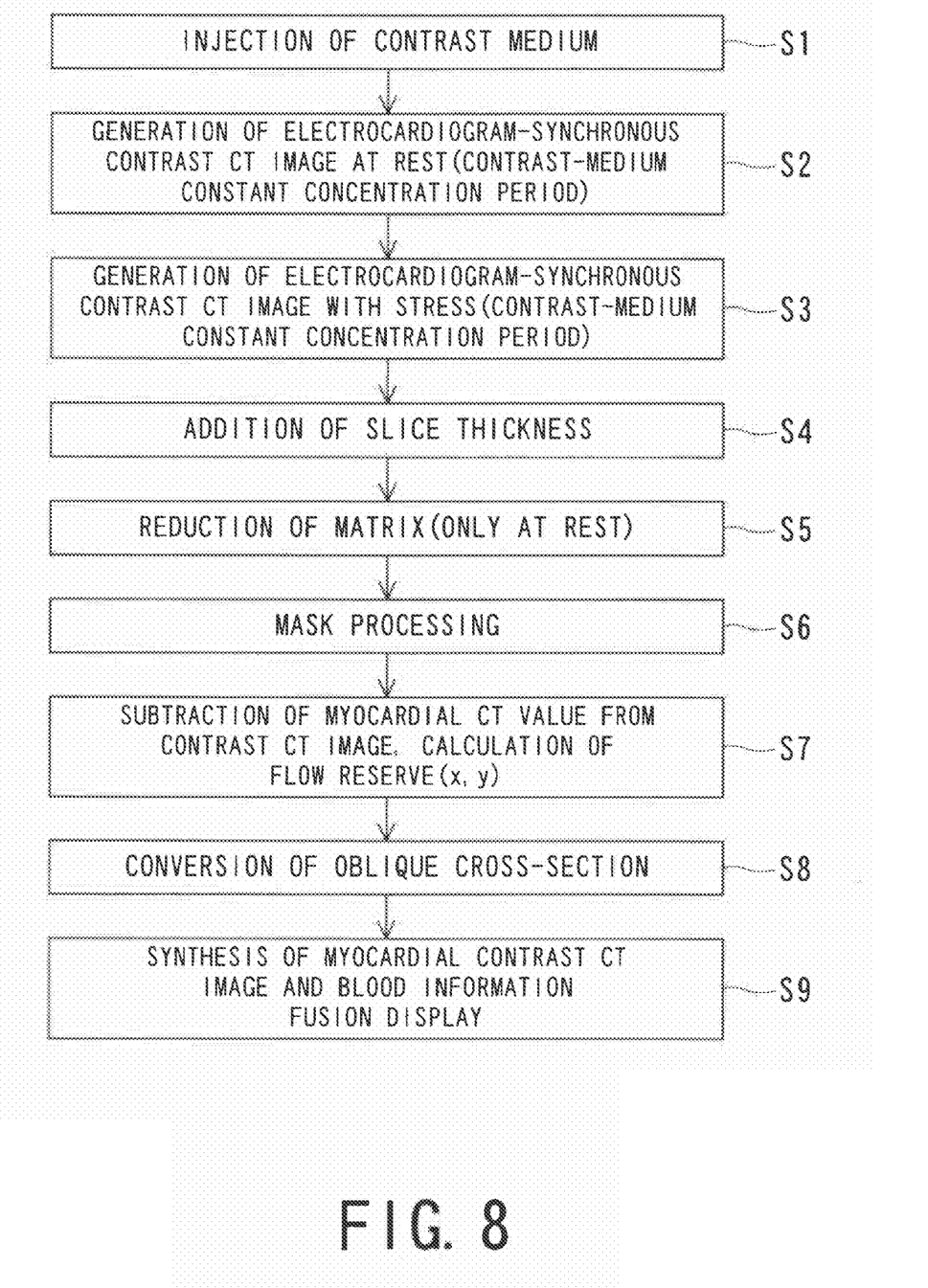
FIG. 8 is a flowchart illustrating a procedures example at the time of obtaining and displaying myocardial blood flow information by the X-ray CT apparatus illustrated in FIG. 1.

FIG. 8 is a flowchart illustrating a procedures example at the time of obtaining and displaying myocardial blood flow information by the X-ray CT apparatus 1 illustrated in FIG. 1, wherein reference characters made up of a character S and a number represent each step in the flowchart.

First, in Step S1, the contrast-medium injector 8 is controlled by a control signal from the scanning control device 18, a contrast medium is continuously injected into the object P in accordance with a certain condition from the contrast-medium injector 8, as illustrated in FIG. 4.

Further, the unshown table is stopped by control from the scanning control device 18, and then pre-scanning is performed. In order to know the timing at which the contrast medium reaches the myocardium through sites such as the myocardial left ventricular lumen, contrast CT image data at an arbitrary slice position over the specific myocardial site is dynamically collected synchronously with an electrocardiogram to monitor the specific myocardial site during a transition period in which the contrast medium concentration Cmyo(t) within the myocardial region is sufficiently smaller than the contrast medium concentration Ca(t) within the left ventricular lumen.

More specifically, the electrocardiograph 9 detects an ECG signal via the unshown electrodes bonded to the object P. The electrocardiograph 9 acquires an electrocardiogram and provides this to the scanning control device 18. The scanning control device 18 provides a control signal to the high-voltage generator 5 based on the electrocardiogram acquired by the electrocardiograph 9. Consequently, the high-voltage generator 5 supplies a tube current and tube voltage to the X-ray tube 4 synchronously with an electrocardiography wave, and X-rays are radiated upon the object P.

The X-ray detector 6 detects the X-rays radiated upon the object P and passed through the object P. An X-ray detection signal output from the X-ray detector 6 is provided to the DAS 7, where digitized raw data is generated. The DAS 7 provides the generated raw data to the preprocessing unit 20, and the preprocessing unit 20 subjects the raw data to preprocessing such as various types of correction processing so as to convert the raw data into projection data. The projection data obtained by the preprocessing unit 20 is temporally stored in the memory unit 21, and then provided to the image reconstruction unit 22. The image reconstruction unit 22 reconstructs CT image data from the projection data, and the reconstructed CT image data is recorded and stored in the storage device 23.

Note that the contrast medium is injected into the object P, so the CT image data to be stored in the storage device 23 becomes contrast CT image data. The CT image is collected synchronously with an electrocardiogram, so a myocardial contrast axial cross-sectional image can be obtained at the same period of each myocardial portion in a myocardial reduction or expansion period. The image acquisition unit 24a acquires the contrast CT image data stored in the storage device 23, and provides this to the myocardial perfusion image generating system 24.

Upon the transition period elapsing, the contrast medium concentration Ca(t) within the coronary artery of the object P becomes a state in which the concentration or the temporal change rate is considered to be constant. Moreover, the contrast medium concentration Cmyo(t) within the myocardial portion becomes a state in which the concentration or the temporal change rate is considered to be constant.

Consequently, the scanning control device 18 automatically detects the timing at which the contrast medium reaches the myocardium using the aforementioned arbitrary method. Alternatively, an arrangement may be made wherein an electrocardiogram-synchronous CT image or the time-of-change curve of the contrast medium concentration as illustrated in FIG. 4 is graphically displayed, and the user can visually recognize the timing at which the contrast medium reaches the myocardium.

Next, in Step S2, the scanning control device 18 starts real-scanning at rest with moving the unshown table synchronously with the timing at which certain delay time is elapsed as necessary. The contrast CT image data of the entire myocardium is collected synchronously with an electrocardiogram during a period in which the contrast medium concentration Cmyo(t) within the myocardial portion at rest is considered to be constant.

Next, in Step S3, the scanning control device 18 starts real-scanning with drug stress with moving the unshown table synchronously with the timing at which certain delay time is elapsed as necessary. The contrast CT image data of the entire myocardium is collected synchronously with an electrocardiogram during a period in which the contrast medium concentration Cmyo(t) within the myocardial portion with drug stress is considered to be constant.

The myocardial perfusion image generating system 24 can generate a blood flow image and blood flow information such as flow reserve (x, y) from the myocardial contrast CT image data thus collected at rest and with drug stress.

Now, attempting to generate a blood flow image and blood flow information without changing the resolution of the myocardial contrast CT image data may allow influence of noise. Consequently, the myocardial contrast CT image data is subjected to resolution reduction processing in a specific direction as preprocessing of generating a blood flow image and blood flow information as necessary.

More specifically, in Step S4, the slice-thickness adder unit 24b receives myocardial contrast CT image data at rest and with drug stress from the image acquisition unit 24a, and adds or averages the contrast CT values in the adjacent multiple slices, thereby performing the resolution reduction processing of the contrast CT image data in the slice direction z. For example, the slice thickness of the myocardial contrast CT image is normally 0.5 mm or so, so in order to employ the myocardial contrast CT image data for generating a blood flow image and blood flow information, the resolution in the slice direction z is reduced wherein the slick thickness becomes 3 mm, 5 mm, or 10 mm or so.

Furthermore, in Step S5, the matrix reduction unit 24c adds the contrast CT values of the myocardial contrast CT image data in each slice, or averages thereof, thereby performing matrix reduction processing. That is, smoothing processing is performed in the x, y directions parallel to a slice to contrast CT image data to be used for the calculation of a blood flow image or a flow reserve (x, y) at rest.

Note that, the processing order of slice-thickness addition processing and matrix reduction processing may be in reverse order, it is arbitrary.

Next, in Step S6, when the resolution reduction processing is complete, the mask processing unit 24d subjects the myocardial contrast CT image data at rest and with drug stress to masking, thereby extracting regions including the blood flow, of the myocardial contrast CT image data.

Subsequently in Step S7, the blood-flow information generating unit 24e subtracts the CT value a of the myocardium from the contrast CT image data at rest and with drug stress included in the regions where the blood flow exists following the masking processing, and concentrations Cmyo(x,y,t1), Cmyo(x,y,t2) of the contrast medium in a myocardium, which correspond to blood flow relative images, are generated. In addition, a flow reserve (x, y) is calculated based on the concentrations Cmyo(x, y, t1), Cmyo(x, y, t2) of the contrast medium on the myocardium. As mentioned above, the concentration Ca(t1) and Ca(t2) of the contrast medium in the LV and a transforming function f(MBA) can be used for the calculation of the flow reserve (x, y).

Figure 9:
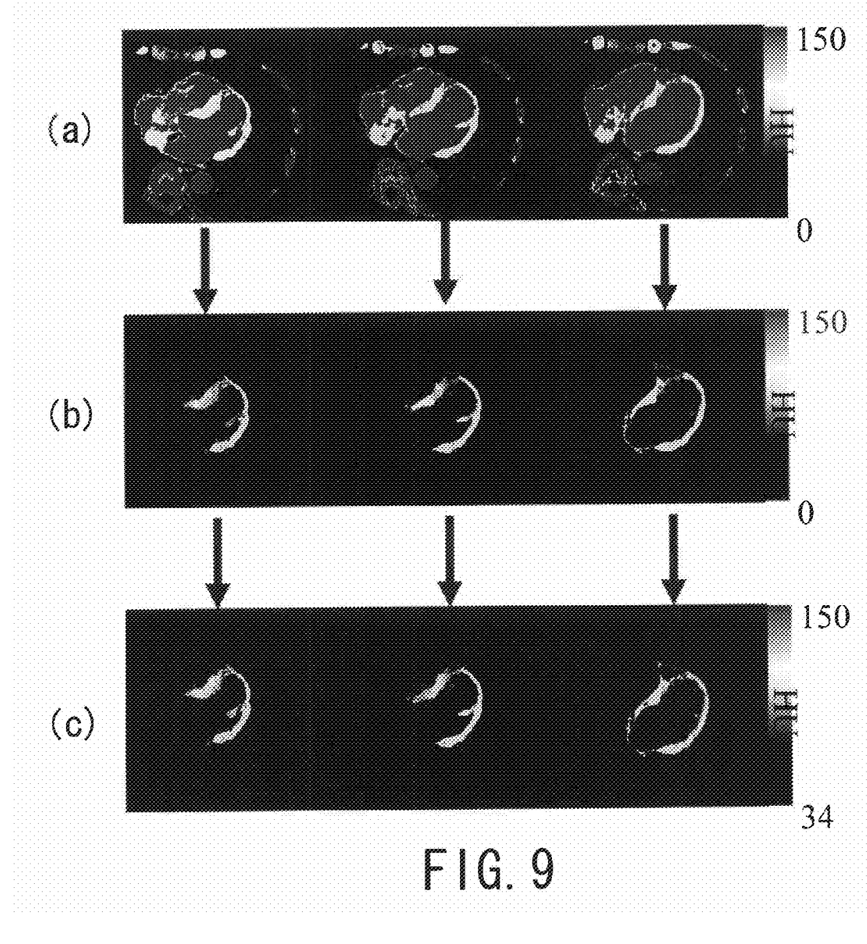
FIG. 9 is a diagram illustrating procedures for generating a blood flow relative image from myocardial contrast CT image data using the X-ray CT apparatus illustrated in FIG. 1, and the obtained blood flow relative image.

FIG. 9 is a diagram illustrating procedures for generating a blood flow relative image from myocardial contrast CT image data using the X-ray CT apparatus illustrated 1 in FIG. 1, and the obtained blood flow relative image.

In FIG. 9, (a) is the myocardial contrast CT image data in each slice following the processing of resolution reduction. The mask processing unit 24d subjects the myocardial contrast CT image data such as shown in (a) to masking, the regions including the blood flow such as shown in (b) are extracted. Here, (b) is an example subjected to masking so that the CT values become between 0 and 150 centered on the left ventricle myocardium. The extracted regions including the blood flow can be recognized from (b).

Furthermore, as illustrated in (b), the blood-flow information generating unit 24e executes subtraction of the CT value of the myocardium from the extracted contrast CT image data, thereby obtaining a image of contrast medium component. Moreover, (c) is the image of contrast medium component obtained by the subtraction processing due to the blood-flow information generating unit 24e, i.e., a myocardial perfusion image example wherein the CT value of the myocardium is set to 34, and is subtracted from the contrast CT image data uniformly. This calculation removes myocardial components from the image.

In the event that the contrast medium concentration Ca(t) within the coronary artery is not considered to be constant, the blood-flow information generating unit 24e obtains the correction coefficient α(t) as shown in Expression (14), and multiplies the image of contrast medium component by the correction coefficient α(t) so as to correct the image.

Next, as needed, the blood-flow information generating unit 24e converts the myocardial perfusion relative values into blood flow perfusion absolute values based on the contrast CT image data at the slice position over the specific myocardial site A dynamically collected during the concentration transition period Tt. More specifically, first, the blood-flow information generating unit 24e obtains the contrast medium concentration Ca(t) within the left ventricular lumen and the contrast medium concentration Cmyo(t) within the specific myocardial site A at time t during the concentration transition period Tt from the electrocardiogram-synchronous CT image dynamically collected during the concentration transition period Tt.

The approximate expression shown in Expression (2) is satisfied during the concentration transition period Tt, so the blood-flow information generating unit 24e obtains K1 at the specific myocardial site A from the contrast medium concentration Ca(t) within the left ventricular lumen and the contrast medium concentration Cmyo(t) within the specific myocardial site A using Expression (5) due to a technique called as the Patlak pilot method. Subsequently, the blood-flow information generating unit 24e obtains K1a/(E×Ra) from the value K1a of K1 at the specific myocardial site A and the relative value Ra of the blood flow perfusion F, and multiplies the relative value R of the blood flow perfusion F at the corresponding site by K1a/(E×Ra), thereby obtaining the absolute value of the blood flow perfusion F. Consequently, the blood flow absolute image can be obtained from the blood flow relative image.

Note that the blood flow absolute image and the blood flow relative image are essentially the same from the perspective of display, and the difference between both is only in that the pixel values assigned to the blood flow absolute image are correlated with the absolute values of the blood flow perfusion F.

There is relevance such as value continuity between the intensity of the blood flow absolute image at the corresponding site and that of the image of the myocardial portion in the tomograph of another myocardial perfusion, so the blood-flow information generating unit 24e also multiplies the absolute value R of the blood flow perfusion F within another myocardial cross-section by K1a/(E×Ra) in the same way, so as to convert the relative value R of the blood flow perfusion F regarding the tomograph of the entire myocardium into the absolute value of the blood flow perfusion F. Thus, the blood-flow information generating unit 24e converts the blood flow image at the myocardium from the absolute values to the relative values, and then obtains the distribution image of the local myocardial blood flow absolute values over the entire myocardium.

The myocardial perfusion image and the flow reserve (x, y) thus generated are employed for diagnosis. Furthermore, the myocardial perfusion image and the flow reserve (x, y) are subjected to various types of processing for facilitating diagnosis as necessary.

For example, in Step S8, the oblique cross-section converting unit 24f subjects the cross-section of the myocardial perfusion image and/or the flow reserve (x, y) to conversion processing so as to generate the oblique cross-sectional image of the myocardial fusion image or the flow reserve (x, y) Note that this Step S8 may be performed following Step S3.

Furthermore, convenience at the time of diagnosis can be improved by synthesizing the myocardial perfusion image and/or the flow reserve (x, y) with the myocardial image for display.

Consequently, in Step S9, the image synthesizing unit 24g receives the high-resolution myocardial image prior to the matrix reduction processing and the addition of the contrast CT values between slices from the image acquisition unit 24a, and generates an image synthesized with the myocardial perfusion image and/or the flow reserve (x, y).

The respective images such as the blood flow image and the flow reserve (x, y) generated by the blood-flow information generating unit 24e, the oblique cross-sectional image generated by the oblique cross-section converting unit 24f, and the synthesized image generated by the image synthesizing unit 24g are provided to the display processing unit 24h. Subsequently, the display processing unit 24h provides image signals for displaying each image to the image display unit 16 so as to display the image signals.

Thus, for example, a contrast CT image on the myocardial region at rest, a contrast CT image on the myocardial region with drug stress and a flow reserve (x, y) as shown in FIG. 5 and FIG. 7 can be also displayed in parallel as blood flow information respectively on the image display unit 16.

Figure 10:
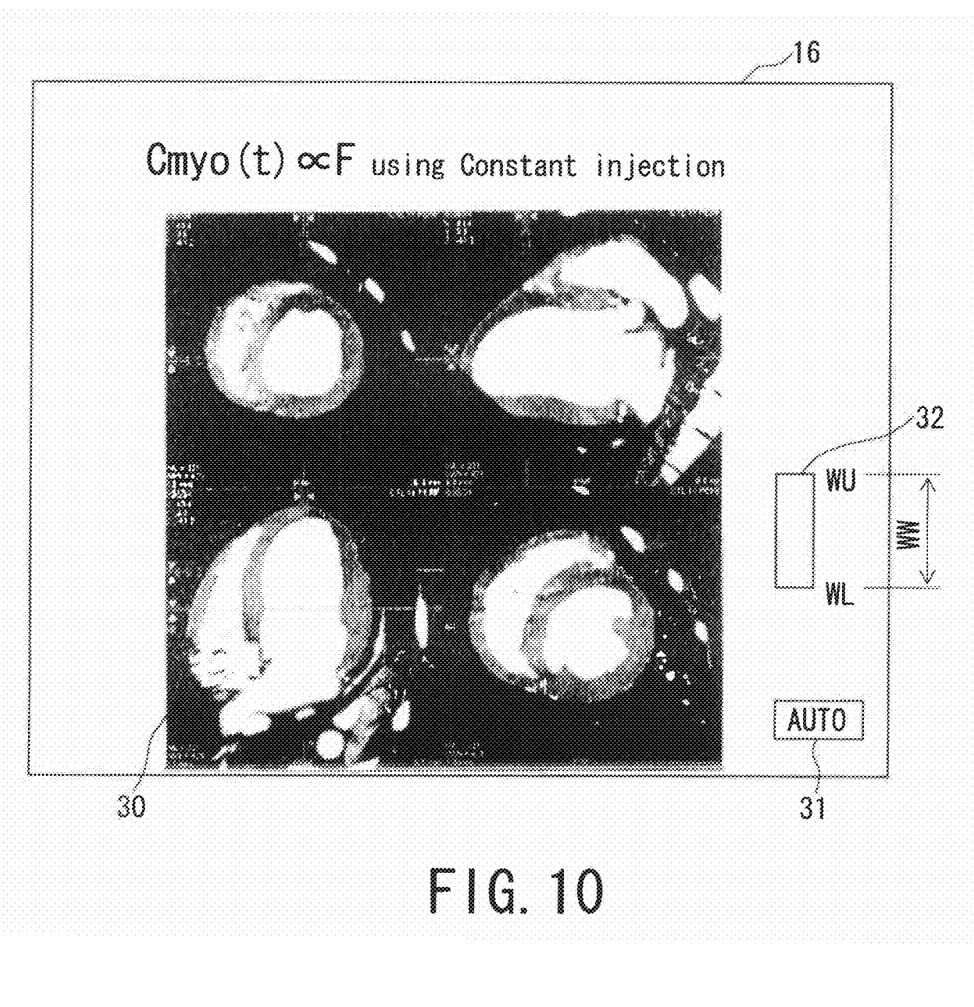
FIG. 10 is a diagram illustrating a flow reserve (x, y) example displayed on the image display unit of the X-ray CT apparatus illustrated in FIG. 1 by automatically setting display conditions.

FIG. 10 is a diagram illustrating a flow reserve (x, y) example displayed on the image display unit 16 of the X-ray CT apparatus 1 illustrated in FIG. 1 by automatically setting display conditions.

As illustrated in FIG. 10, a flow reserve (x, y) 30, an automatic (AUTO) button 31 for instructing automatic setting of display conditions, and a luminance scale 32 are displayed on the screen of the image display unit 16. That is to say, FIG. 10 illustrates an example in the case of displaying the flow reserve (x, y) by luminance so as to recognize the image through the grayscale. Note that, in FIG. 10, another portion is superposed and displayed on the flow reserve (x, y) in the myocardial portion.

Upon the user pressing the automatic (AUTO) button 31 by operating the input unit 17, the input unit 17 provides the automatic setting instructions of display conditions to the display processing unit 24h. In response to the instructions, the display processing unit 24h sets an appropriate value to an upper limit value WU and lower limit value WL of the luminance scale (window level), and the a width of window level WW between upper limit value and lower limit value to display a flow reserve (x, y) automatically.

In addition to this, displaying the range between WU and WL in color may allow the user to visually recognize the flow reserve (x, y) of the myocardial portion. In the event of performing color display, gradation of color display may be divided into 16 stages visually, or may be divided into 16 stages or more, or 16 stages or less, according to stages to be recognized, for example.

The X-ray CT apparatus 1 and the myocardial perfusion information generating system 24 as described above are apparatuses to acquire contrast CT images during the contrast medium constant concentration period with drug stress and at rest respectively, to obtain blood flow information typified by flow reserve for diagnosis from blood flow information included in the contrast CT images with drug stress and at rest respectively and to display it.

Accordingly, the X-ray CT apparatus 1 and the myocardial perfusion image generating system 24 generate blood information useful for diagnosis in shorter a period while further reducing the contrast medium injection rate as to the object and dosage due to X-rays. In other words, heretofore, scanning for acquiring a myocardial image and scanning for acquiring blood flow information have been performed independently, but the X-ray CT apparatus 1 and myocardial perfusion image generating system 24 can acquire useful blood flow information from information, such as the coronary artery contrast CT image data, myocardial contrast CT image data, and the like, obtained by the scanning for acquiring a myocardial image without adding the scanning for acquiring the blood flow information.

Note that with the aforementioned embodiment, blood flow information such as a blood flow image and flow reserve has been generated by subtracting the CT value of the myocardium alone from the myocardial contrast CT image data, but blood flow information such as a blood flow image and flow reserve may be generated by subtracting a value obtained by adding/subtracting/multiplying/dividing a certain value as to the CT value of the myocardium, i.e., a certain value obtained from the CT value of the myocardium from the myocardial contrast CT image data.

Not only flow reserve but also other blood flow information helpful for diagnosis may be obtained from blood flow information at rest and at non-rest of an object.

What is claimed is:

1. An X-ray CT apparatus comprising:
an image generating unit configured to acquire projection data at rest and projection data at non-rest from a myocardial part of an object into which contrast medium is injected continuously at the rest and at the non-rest respectively in a state in which each concentration of the contrast medium is constant and reconstruct contrast CT image data at the rest and contrast CT image data at the non-rest using the acquired projection data at the rest and the acquired projection data at the non-rest respectively; and
a blood flow information acquiring unit configured to obtain third blood flow information based on first blood flow information derived from the contrast CT image data at the rest and second blood flow information derived from the contrast CT image data at the non-rest.

2. An X-ray CT apparatus of claim 1,
wherein said blood flow information acquiring unit is configured to obtain a flow reserve as the third blood flow information.

3. An X-ray CT apparatus of claim 1,
wherein said blood flow information acquiring unit is configured to obtain a flow reserve as the third blood flow information by calculating a ratio between a concentration of the contrast medium of the myocardial part at the rest and a concentration of the contrast medium of the myocardial part at the non-rest.

4. An X-ray CT apparatus of claim 1,
wherein said blood flow information acquiring unit is configured to obtain a flow reserve as the third blood flow information based on a concentration of the contrast medium of the myocardial part at the rest and a concentration of the contrast medium of the myocardial part at the non-rest by amending the concentration of the contrast medium of the myocardial part at the rest and the concentration of the contrast medium of the myocardial part at the non-rest with concentrations of the contrast medium at the rest and the non-rest in a heart lumen or a coronary artery.

5. An X-ray CT apparatus of claim 1,
wherein said blood flow information acquiring unit includes a transforming unit configured to obtain the third blood flow information having a nonlinear correspondence relationship with a concentration ratio between the contrast medium in the myocardial part and the contrast medium in a heart left ventricular lumen or a coronary artery based on the concentration ratio.

6. An X-ray CT apparatus of claim 1,
wherein said blood flow information acquiring unit is configured to obtain a flow reserve as the third blood flow information by calculating a concentration ratio between the contrast medium in the myocardial part and the contrast medium in a heart left ventricular lumen or a coronary artery at the rest and a concentration ratio between the contrast medium in the myocardial part and the contrast medium in the heart left ventricular lumen or the coronary artery at the non-rest.

7. An X-ray CT apparatus of claim 1,
wherein said blood flow information acquiring unit is configured to obtain a flow reserve as the third blood flow information by calculating a ratio between a value derived by substituting a concentration ratio of the contrast medium at the rest into an inverse function of a transforming function and a value derived by substituting a concentration ratio of the contrast medium at the non-rest into the inverse function of the transforming function, the concentration ratio of the contrast medium at the rest being defined as a concentration ratio between the contrast medium in the myocardial part and the contrast medium in a heart left ventricular lumen or a coronary artery at the rest, the concentration ratio of the contrast medium at the non-rest being defined as a concentration ratio between the contrast medium in the myocardial part and the contrast medium in the heart left ventricular lumen or the coronary artery at the rest, the transforming function being a function for transforming a myocardial blood flow into a concentration ratio between the contrast medium in the myocardial part and the contrast medium in the heart left ventricular lumen or the coronary artery.

8. An X-ray CT apparatus of claim 1,
wherein said blood flow information acquiring unit is configured to obtain the third blood flow information using smoothed first blood flow information by smoothing the first blood flow information in at least one direction on a myocardial short axis crossing image.

9. An X-ray CT apparatus of claim 1, further comprising:
a display unit configured to display the first blood flow information, the second blood flow information and the third blood flow information.

10. A myocardial perfusion information generating system comprising:
an image acquiring unit configured to acquire contrast CT image data at a rest and contrast CT image data at a non-rest of a myocardial part of an object into which contrast medium is injected continuously in a state in which each concentration of the contrast medium at the rest and at the non-rest is constant respectively; and
a blood flow information acquiring unit configured to obtain third blood flow information based on first blood flow information derived from the contrast CT image data at the rest and second blood flow information derived from the contrast CT image data at the non-rest.

11. An X-ray diagnostic method comprising:
acquiring projection data at rest and projection data at non-rest from a myocardial part of an object into which contrast medium is injected continuously at the rest and at the non-rest respectively in a state in which each concentration of the contrast medium is constant and reconstructing contrast CT image data at the rest and contrast CT image data at the non-rest using the acquired projection data at the rest and the acquired projection data at the non-rest respectively; and
obtaining third blood flow information based on first blood flow information derived from the contrast CT image data at the rest and second blood flow information derived from the contrast CT image data at the non-rest.

12. A myocardial perfusion information generating method comprising:
acquiring contrast CT image data at a rest and contrast CT image data at a non-rest of a myocardial part of an object into which contrast medium is injected continuously in a state in which each concentration of the contrast medium at the rest and at the non-rest is constant respectively; and
obtaining third blood flow information based on first blood flow information derived from the contrast CT image data at the rest and second blood flow information derived from the contrast CT image data at the non-rest.

* * * * *